US00PP20649P3

(12) United States Plant Patent

McGranahan et al.

(10) Patent No.: US PP20,649 P3
(45) Date of Patent: Jan. 19, 2010

(54) WALNUT ROOTSTOCK 'RX1'

(50) Latin Name: *Juglans microcarpa×Juglans regia*
Varietal Denomination: RX1

(75) Inventors: Gale McGranahan, Davis, CA (US); Gregory Browne, Davis, CA (US); Charles Leslie, Davis, CA (US); Wesley Hackett, Davis, CA (US); James McKenna, Davis, CA (US)

(73) Assignees: The Regents of the University of California, Oakland, CA (US); The United States of America, as represented by the Secretary of Agriculture, Washington, DC (US)

( * ) Notice: Subject to any disclaimer, the term of this patent is extended or adjusted under 35 U.S.C. 154(b) by 64 days.

(21) Appl. No.: 11/821,845
(22) Filed: Jun. 25, 2007

(65) Prior Publication Data
US 2008/0320619 P1 Dec. 25, 2008

(51) Int. Cl.
*A01H 5/00* (2006.01)

(52) U.S. Cl. ..... Plt./154

(58) Field of Classification Search ..... Plt./154
See application file for complete search history.

(56) References Cited

OTHER PUBLICATIONS

McGranahan, Gail. Nurseries Licensed to Sell New Clonal Rootstocks. May 1, 2008 available at: http://cesutter.ucdavis.edu/files/51594.pdf.*
McGranahan, G. et al. (1996). "The Paradox Diversity Study," Walnut Research Reports 1996, pp. 43-48.
Browne, G.T. et al. (1998). "Strategies For Control of Phytophthora Root and Crown Rots of Walnut," Walnut Research Reports 1997, pp. 381-391.
McGranahan, G. et al. (1998). "The Paradox Diversity Study," Walnut Research Reports 1997, pp. 55-63.
Browne, G.T. et al. (1999). "Strategies for Control of Phytophthora Root and Crown Rots of Walnut," Walnut Research Reports 1998, pp. 361-371.
McKenna, J. et al. (1999). "The Paradox Genetic Diversity Study," Walnut Research Reports 1998, pp. 40-65.
Browne, G. (2001). "Strategies for Management of Phytophthora on Walnut: Evaluating Potential of Elite Paradox Clones and Wingnut Families," Walnut Research Reports 2000, pp. 429-436.
McKenry, M. et al. (2001). "A Three-Year Search for Nematode Resistance in Walnut-Final Report," Walnut Research Reports 2000, pp. 509-512.
Browne, G. (2002). "Strategies for Management of Phytophthora on Walnut: Evaluating Potential of Elite Paradox Clones and Wingnut Families," Walnut Research Reports 2001, pp. 101-109.
Hackett, W.P. et al. (2003). "Propagation and Retesting of Walnut Rootstock Genotypes Putatively Resistant to Pests and Diseases," Walnut Research Reports 2002, pp. 99-107.
Browne, G.T. et al. (2004). "Evaluation of Resistance to Phytophthora citricola Among Diverse Clones of Paradox Hybrid Rootstocks," Proceedings of the Vth International Walnut Symposium, Sorrento, Italy, pp. 395-405.
Hackett, W.P. et al. (2004). "Propagation and Retesting of Walnut Rootstock Genotypes Putatively Resistant to Pests and Diseases," Walnut Research Reports 2003, pp. 85-95.
McKenry, M. (2004). "Field Evaluations/Inputs for Grower Replant Settings and New Lines of Nematode Resistance," Walnut Research Reports 2003, pp. 431-439.
Browne, G. et al. (2005). "Determining Phytophthora Resistance in Elite Paradox Clones and Specific Etiology of a Paradox Crown and Root Rot," Walnut Research Reports 2004, pp. 379-387.
Hackett, W.P. et al. (2005). "Propagation and Retesting of Walnut Rootstock Genotypes Putatively Resistant to Pests and Diseases," Walnut Research Reports 2004, pp. 89-95.
McKenry, M. (2005). "Field Evaluations/Inputs for Grower Replant Settings and New Lines of Nematode Resistance," Walnut Research Reports 2004, pp. 407-415.
McKenry, M. (2006). "Field Evaluations/Inputs for Grower Replant Settings and New Lines of Nematode Resistance," Walnut Research Reports 2005, pp. 365-371.
McGranahan, G. et al. (2006). "Clonal Propagation of Walnut Rootstock Genotypes for Genetic Improvement," Walnut Research Reports 2005, pp. 85-93.
Browne, G. et al. (2006). "Biology and Management of Phytophthora Crown and Root Rot of Walnut," Walnut Research Reports 2005, pp. 335-344.
McKenry, M. (2007). "Filed Evaluations/Inputs for Grower Replant Settings and New Lines of Nematode Resistance," Walnut Research Reports 2006, pp. 279-283.
Grant, J. et al. (2007). "Orchard Performance of Selected Clonal Paradox Rootstocks," Walnut Research Reports 2006, pp. 79-81.
McGranahan, G. et al. (2007). "Clonal Propagation of Walnut Rootstock Genotypes for Genetic Improvement 2006," Walnut Research Reports 2006, pp. 71-78.
Browne, G. T. et al. (1999-2000). Project Plan/Research Grant Proposal for Year 4 of 5 of "Strategies for Control of Phytophthora Root and Crown Rots of Walnut," University of California Division of Agricultural Sciences, 6 pages.
Browne, G. T. et al. (2000-2001). Project Plan/Research Grant Proposal for "Strategies for Management of Phytophthora Crown and Root Rots: Evaluating Potential of Elite Paradox Clones and Wingnut Families," University of California Division of Agricultural Sciences, 5 pages.
Browne, G. T. et al. (2001-2002). Project Plan/Research Grant Proposal for Year 2 of 3 of "Strategies for Management of Phytophthora Crown and Root Rots: Evaluating Potential of Elite Paradox Clones and Wingnut Families," University of California Division of Agricultural Sciences, 5 pages.
Browne, G. T. et al. (2004-2005). Project Plan/Research Grant Proposal for Year 1 of 2 of "Determining Phytophthora Resistance in Elite Paradox Clones and Specific Etiology of a Paradox Crown and Root Rot," University of California Division of Agricultural Sciences, 5 pages.
* cited by examiner

*Primary Examiner*—Wendy C. Haas
(74) *Attorney, Agent, or Firm*—Morrison & Foerster LLP

(57) ABSTRACT

A new and distinct variety of walnut rootstock denominated 'RX1' is described. This new variety, 'RX1', can be propagated through standard tissue culture micropropagation. It has excellent survivability in the nursery and orchard. The new variety also has reduced susceptibility to damage from *Phytophthora citricola* in greenhouse screens and in the field compared to other available walnut rootstocks.

9 Drawing Sheets

FIELD OF THE INVENTION

Botanical/commercial classification: *Juglans microcarpa×Juglans regia*/new walnut rootstock. Varietal denomination: 'RX1'.

BACKGROUND OF THE INVENTION

The present invention relates to a new and distinct clonal rootstock for English walnut (*Juglans regia*) that has been denominated varietally as 'RX1', and more particularly to such a walnut rootstock that has reduced susceptibility to cankering by *Phytophthora* (*Phytophthora citricola*), and that further is easily clonally propagated by micropropagation.

It has long been recognized that *Phytophthora* root and crown rots are some of the most serious diseases of walnut worldwide. In California, *Phytophthora citricola* and *P. cinnamomi* are recognized as the most virulent species of the fungus, but *P. citricola* is more widespread. The rootstock of the present invention, 'RX1', has been identified as being more resistant to *P. citricola* than other available clonal walnut (*Juglans*) rootstocks.

SUMMARY OF THE INVENTION

It was found that the walnut rootstock 'RX1' of the present invention exhibits the following combination of characteristics:

a) can be propagated through standard tissue culture micropropagation;
b) has excellent survivability in the nursery and orchard; and
c) has reduced susceptibility to damage from *Phytophthora citricola* in greenhouse screens and in the field compared to other available walnut rootstocks.

BRIEF DESCRIPTION OF THE TABLES

Table 1 shows comparative nursery performance of 'RX1' and other rootstock clones grown in Stanislaus County, Calif. in 2004.

Table 2 shows comparative nursery performance of 'RX1' and other rootstock clones grown at in Butte County, Calif. in 2004.

Table 3 shows field performance of 'RX1' and other clonal and seedling rootstocks in non-infested soil and soil infested with *Phytophthora citricola.*

DETAILED DESCRIPTION OF THE INVENTION

The new rootstock, 'RX1' was selected as part of the "Paradox Diversity Study" (PDS) which was initiated in 1996 to study the genetic diversity of commercial walnut rootstocks. The hybrid of *J. hindsii*×*J. regia,* commonly known as 'Paradox' (not patented), is the most frequently planted rootstock for English walnut in California. The study included approximately 300–500 seed (depending on the predicted percent 'Paradox'), from 37 black walnut sources of 'Paradox' supplied by California walnut nurseries, and 7 controlled crosses and open-pollinated controls from several different walnut species including Texas black, *Juglans microcarpa.* Seed or seedlings were distributed to cooperating researchers for tests of response to nematodes (*Pratylenchus vulnus*), *Phytophthora* (seed supplied), crown gall (*Agrobacterium tumefaciens*) and the orchard environment (field trials). The study was repeated in 1997.

In fall of 1997, seed from a *Juglans microcarpa* designated as DJUG 29.11 in location B6-3 at the National Germplasm Repository, Davis and growing in Winters, Calif. was tested against *Phytophthora citricola.* From results of the previous year, about 50% germination and about 50% hybrids with *J. regia* from this tree was expected. In fact in 1998, germination was better (70%) but percent hybrids were very low (5%). Due to lack of sufficient seedlings for screening, a representative of the *J. microcarpa*×*J. regia* hybrid family was asexually reproduced by standard tissue culture micropropagation in Davis, Calif. The seedling chosen (98-RX-SD8) later became 'RX1'. Thus, 'RX1' originated as a single plant. It was introduced into culture in summer 1998 using the standard tissue culture micropropagation protocol. In fall 1998, the cultures were transferred to a nursery for further multiplication and rooting.

In summer 2001, a replicated trial in the greenhouse to determine the relative susceptibility of 'RX1' to *Phytophthora citricola* was initiated. The clone appeared to have resistance to the pathogen in preliminary tests. In September, 2001, the clone was evaluated for further production of plants. Between 2001 and 2005, 'RX1' was multiplied, rooted and acclimatized for trials for response to *Phytophthora citricola* and for additional field trials. During summers 2002, 2003, 2004, and 2006, plants were transplanted into appropriate containers, grown to appropriate size for screening, grown on appropriate inocula, and subjected to repeated greenhouse experiments to evaluate resistance of 'RX1' and other selected clones to *P. citricola* . Several modifications in propagation and pre-inoculation treatments were made including induction of dormancy of plants and treatment with hormones. 'RX1' was consistently at least moderately resistant to the pathogen (FIGS. 1–4).

Figure 1:
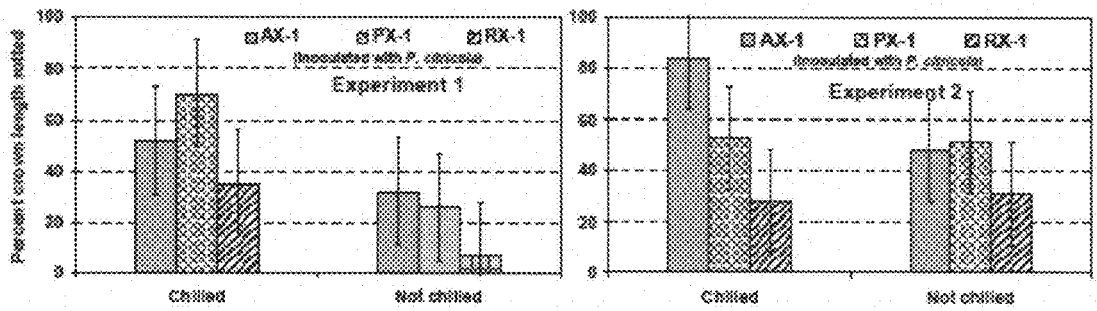
FIG. 1 shows relative susceptibility of 'RX1' and two other potential rootstock clones to *Phytophthora citricola,* and the effect of pre-inoculation chilling on disease severity, 2003 greenhouse screen.
Figure 2:
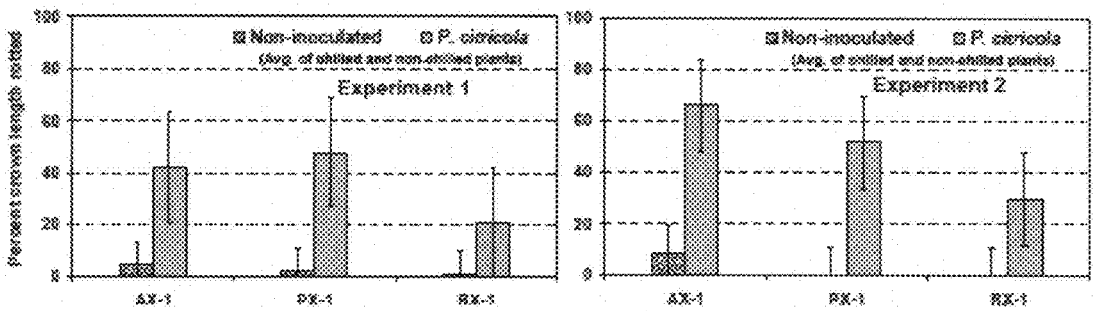
FIG. 2 shows relative susceptibility of 'RX1' and two other potential rootstock clones to *Phytophthora citricola,* data combined for plants subjected to pre-inoculation chilling and non-chilled plants, 2003 greenhouse screen.
Figure 3:
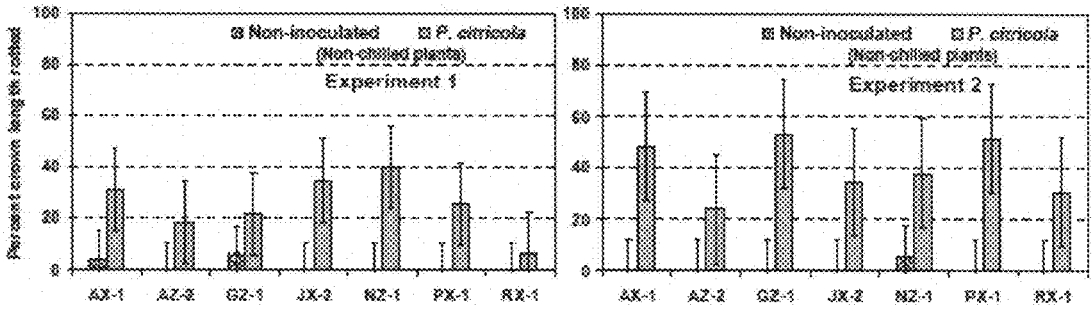
FIG. 3 shows relative susceptibility of 'RX1' and six other potential rootstock clones to *Phytophthora citricola,* 2003 greenhouse screen.
Figure 4:
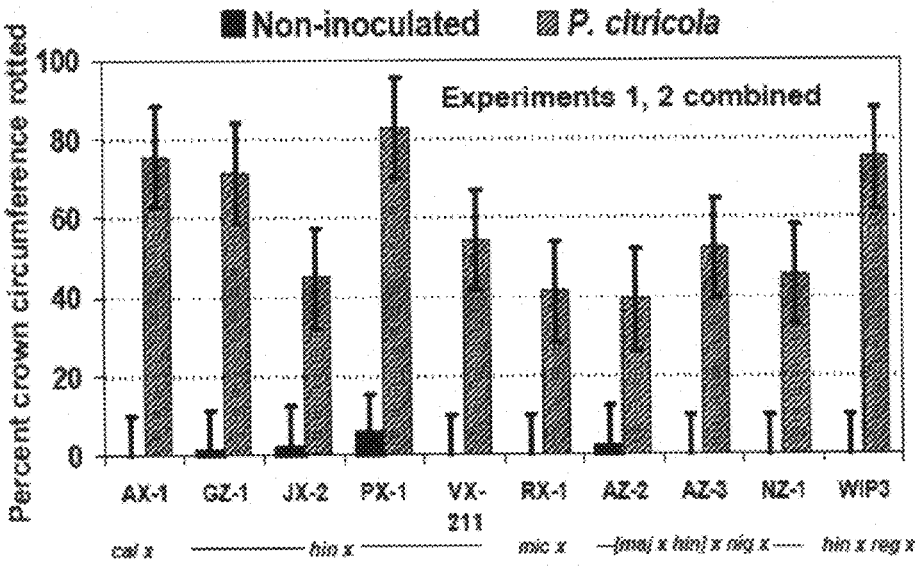
FIG. 4 shows relative susceptibility of 10 hybrid walnut clones to *Phytophthora citricola,* 2004 greenhouse screen.
Figure 5:
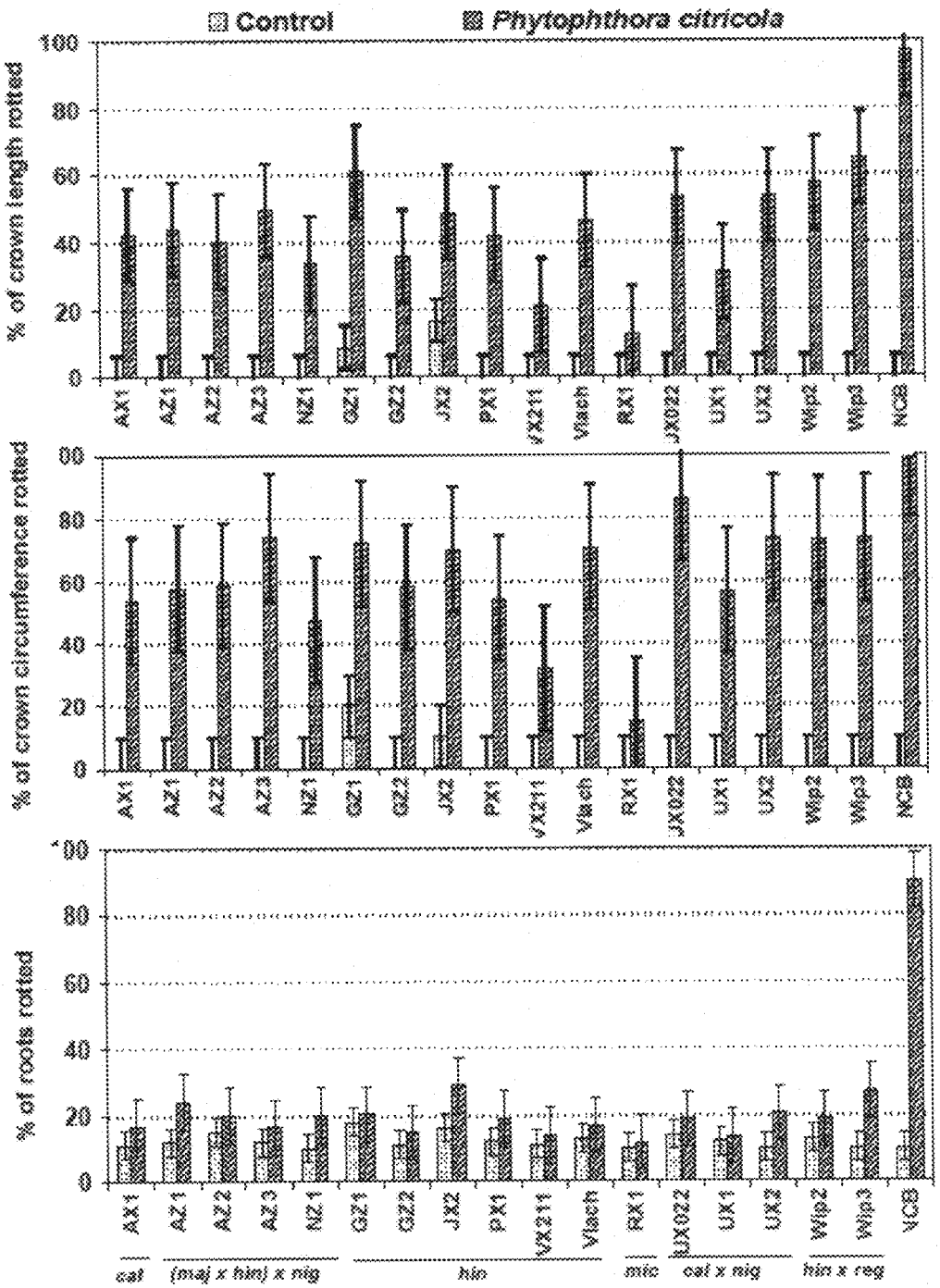
FIG. 5 shows relative susceptibility of 17 hybrid walnut clones and Northern California black walnut to *Phytophthora citricola,* 2006 greenhouse screen.

In August 2006 a screen for *P. citricola* response was conducted with plants of 'RX1' that had been through cycles of dormancy which tended to equalize growth and kept them small enough to facilitate mass screening. The cycles included dormancy induced by storage at 6C for 3–5 months (2004), growth in the greenhouse for one year (2005) and natural dormancy in a lath house followed by growth in the greenhouse (2006). The screen for resistance was initiated in August 2006 by transplanting individual plants from one-liter pots to two-liter pots filled with potting mix soil that was either artificially infested with *P. citricola* (45 ml of *P. citricola*-infested V8 juice-oat-vermiculite substrate per liter of soil) or treated as a control (45 ml sterile substrate per liter of soil). There were 5 replicate plants planted in non-infested soil and 10–20 replicate plants in infested soil, evenly distributed in a split-plot design (main plots were inoculum treatments, subplots were rootstock) among 5 blocks. Every two weeks after transplanting, the soil in each pot was flooded for 48 hours. Three months after transplanting, the root and crown systems were washed free from soil and evaluated visually for incidence and severity of crown and root rot. Among the 17 clonal hybrids evaluated in the screen, 'RX1' was one of the hybrids most resistant to *P. citricola* (FIG. 5).

Figure 6:
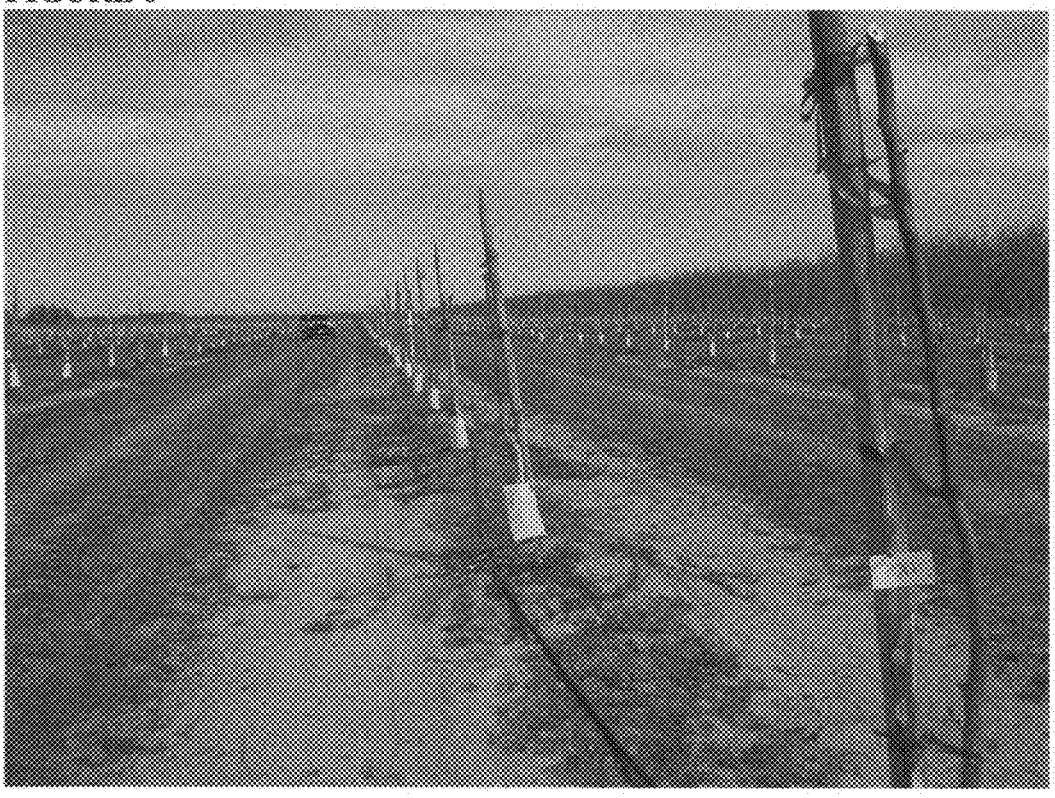
FIG. 6 shows grafted 'RX1' in a new orchard.

During the propagation of plants for *Phytophthora* testing, plants were also being propagated for field trials. These were grown at two nurseries in 2004. 'RX1' was one of the smallest plants at both nurseries (Tables 1 and 2), but produced between 70% and 75% graftable rootstocks as determined by the nursery. These were either grafted in place with 'Chandler' (U.S. Plant Pat. No. 4,388) or distributed for grafted field trials for replant situations or *Phytophthora* field screening in 2005. The 'Chandler'-grafted 'RX1' (n=80) was planted in a new orchard with another promising clone AZ2 (n=80) and seedling 'Paradox' (*J. hindsii*×*J. regia*) provided by the nursery. AZ2 turned out to be a weak clone that could not be transplanted bare root, and survival was very poor after transplanting. Nearly all the 'RX1' survived and were indistinguishable from the seedling 'Paradox' (FIG. 6).

For the *Phytopthora* field trial, 30 each of 11 different genotypes including 'RX1' were planted in May, 2005 in Davis, Calif. and were artificially inoculated with *Phytophthora citricola*. A randomized block split plot design was used. For each rootstock clone, there were six four-tree plots to be infested and six single tree plots to serve as uninoculated controls. Northern California black (*J. hindsii*) and wingnut (*Pterocarya stenoptera*) were included as susceptible and resistant controls, respectively. In January 2006, 100 ml of a V8 juice-oat mixture infested with *P. citricola* was mixed into the upper 5 cm of soil around the trunk of each tree. A sterile mixture was applied to the uninoculated controls.

The block artificially inoculated with *Phytophthora* was assessed for growth in trunk circumference and development of crown rot as indicated by trunk cankers extending up from the soil surface in November 2006. Sixty-two percent of the susceptible controls were rotted or dead. 'RX1' was one of the smaller clones (Table 3), but it was thriving (FIG. 7) and not affected by the inoculation (Table 3).

Preliminary results from grafted field trials suggest that 'RX1' is a survivor in spite of the challenge of being in replant sites (FIGS. 8–11).

BOTANICAL DESCRIPTION OF THE PLANT

This description is based on a 6-month old greenhouse grown clone of 'RX1' produced through standard tissue culture micropropagation, a 3-year old 'RX1' in the *Phytophthora* field screen and a 2-year old RX1 growing in Davis, Calif. Data for the botanical description were collected in spring, 2007.

The Munsell Color Charts for Plant Tissues (1977. Gretag-Macbeth, New Windsor, N.Y.) is used in the identification of color. Also, common color terms are to be accorded their ordinary dictionary significance.

Botanical classification: *Juglans microcarpa*×*Juglans regia.*

Female parent: *Juglans microcarpa*

Male parent: *Juglans regia*

The male parent is identified to be of the species *J. regia,* or English walnut. *J. regia* typically has 7–9 leaflets while *J. microcarpa,* the female patent, typically has 15–23 leaflets. 'RX1' differs from its female parent by having fewer leaflets/leaf, broader leaflets and more vigor. 'RX1' differs from its male parent by having more leaflets/leaf and narrower leaflets.

Figure 7:
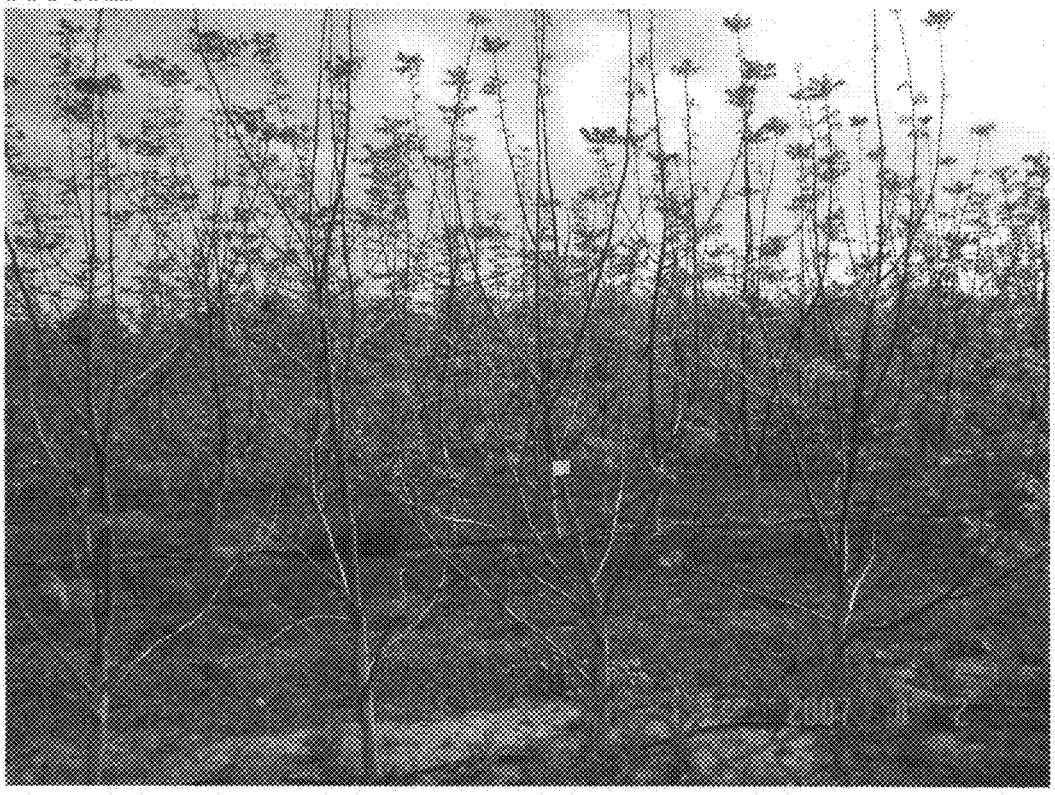
FIG. 7 shows 'RX1' in *Phytophthora* field trial.
Figure 8:
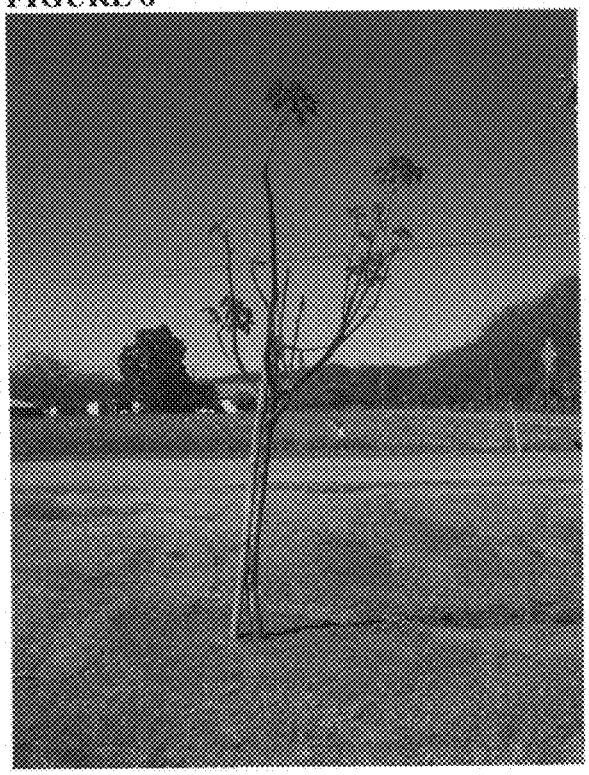
FIG. 8 shows grafted 'RX1' in replant situation.
Figure 9:
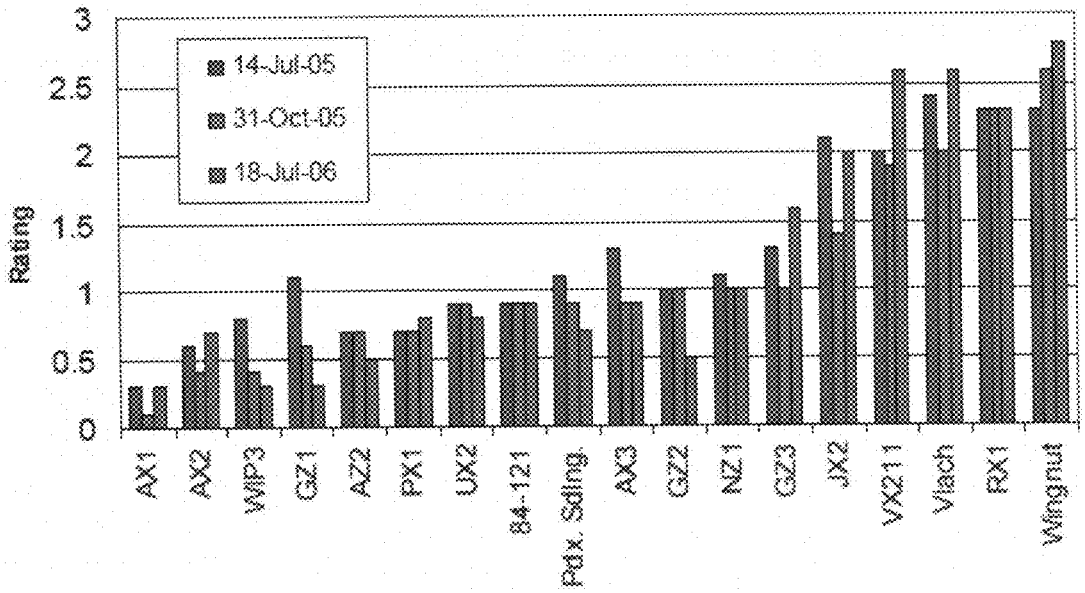
FIG. 9 shows visual rating of tree growth and condition of clonal and seedling test trees at a California field site in 2006.
Figure 10:
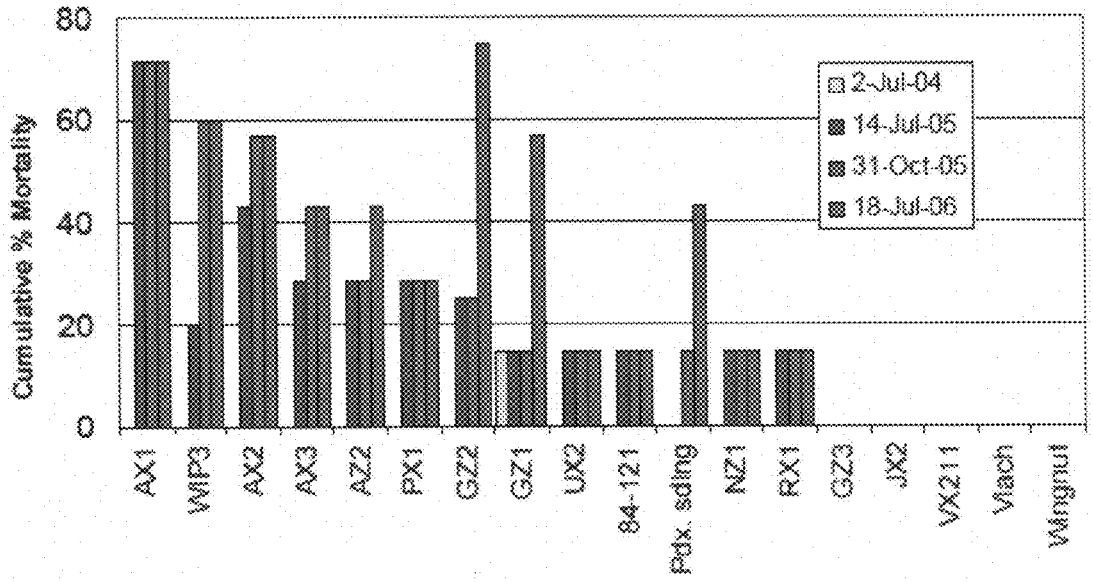
FIG. 10 shows percent mortality for clonal selections and other rootstocks at a California field site.
Figure 11:
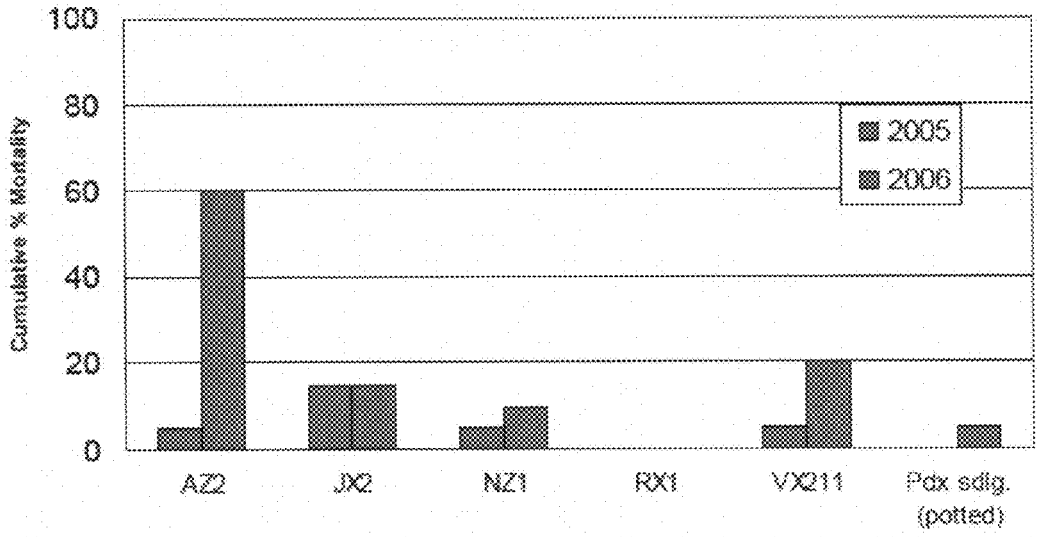
FIG. 11 shows percent mortality for clonal selections and other rootstocks at a California field site.
Figure 12:
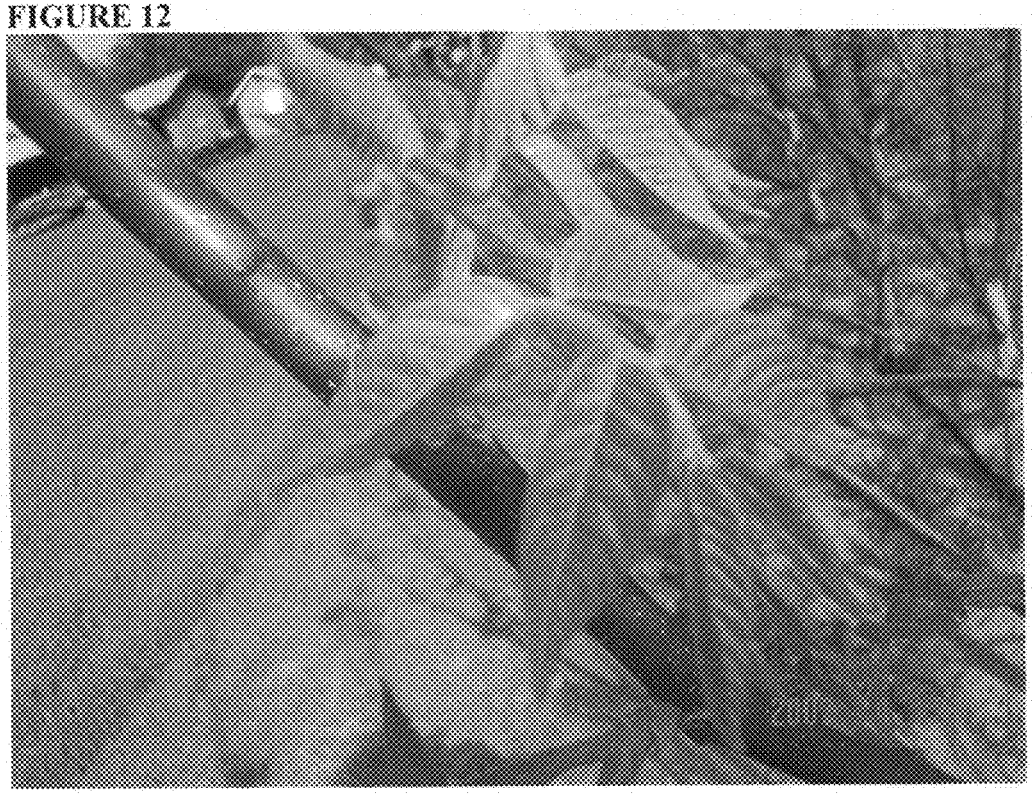
FIG. 12 shows bark and new leaves of three-year old 'RX1' tree.
Figure 13:
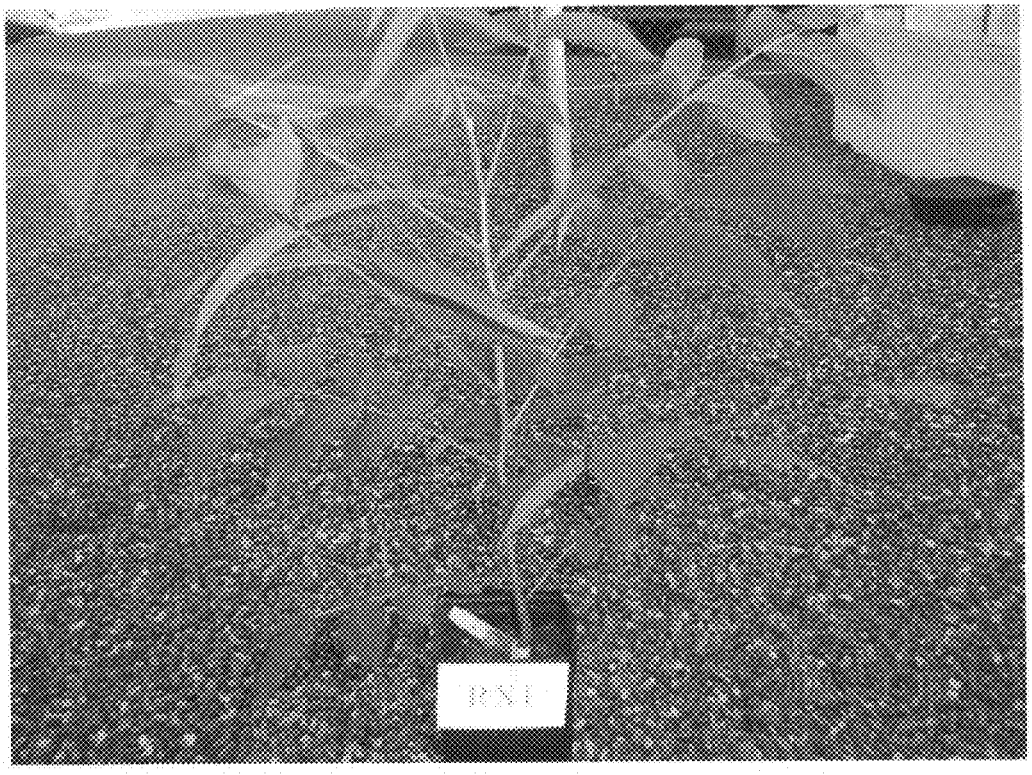
FIG. 13 shows greenhouse grown 'RX1' tree about 6 months old.

Plant: The growth habit of the tree is illustrated in FIG. 7. This 3-year old tree is approximately 3.05 meters tall. Bark of two-year old wood is dark brown (2.5Y 5/2). Bark color of one-year old wood is lighter and redder (7.5YR 5/4) (FIG. 12). Lenticels, about 48 in one square cm, are buff-colored (7.5YR 8/2). The six month old, greenhouse-grown tree is about 45 cm tall with a stem diameter of about 0.8 cm (FIG. 13). The stem is green (5GY 5/10) with scattered lenticels (2.5Y 8/4) more dense towards the base and about 0.5 mm long.

Trunk diameter: 'RX1' is 6.1 meters in height and 11 cm diameter DBH at four years of age.

Figure 14:
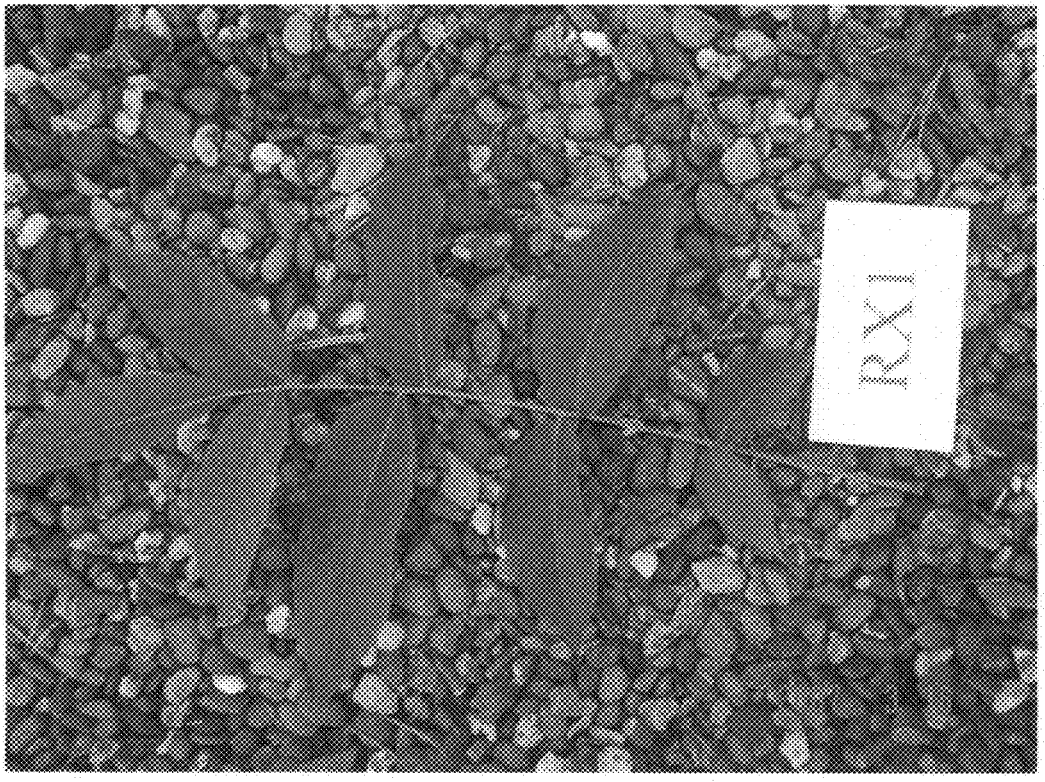
FIG. 14 shows upper side of leaf of 'RX1'.
Figure 15:
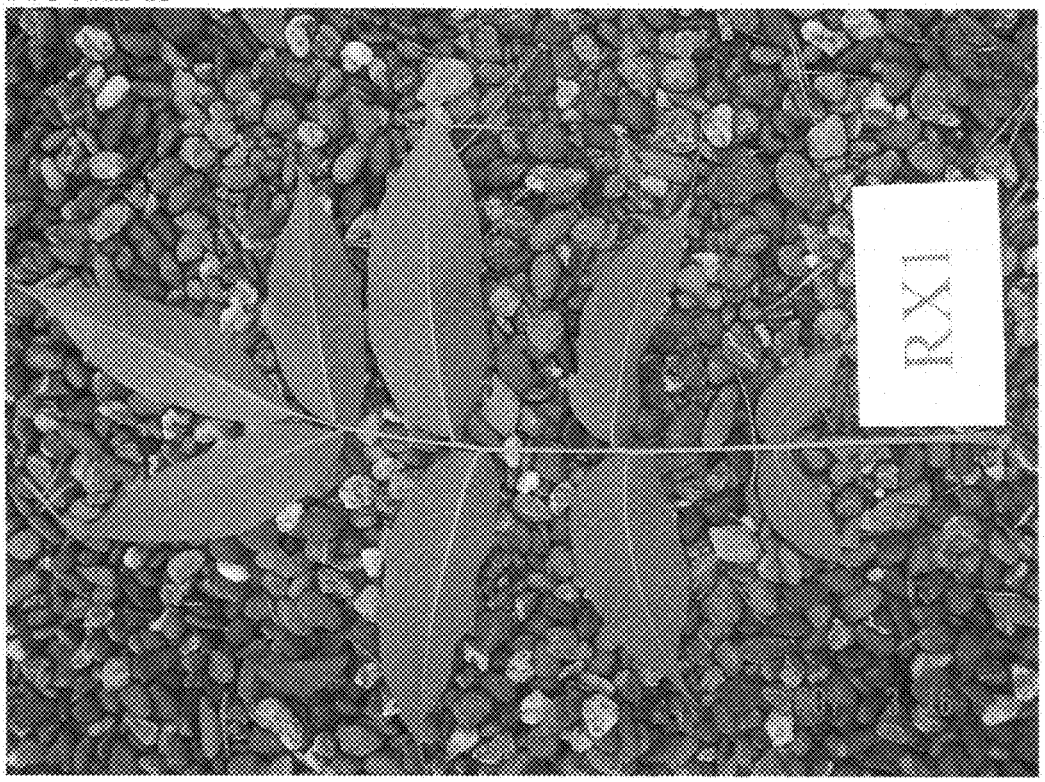
FIG. 15 shows lower side of leaf of 'RX1'.

Foliage: The leaves are pinnately compound and alternate. The slightly pubescent new spring foliage (FIG. 12) has reddish new leaves (10R 5/8) and green older leaves (5GY 5/6). There are 13–15 leaflets. The six-month old greenhouse-grown tree has fewer leaflets (9–11). Leaves are 30 cm long and 28–30 cm wide with petioles 5–8 cm long. Leaflets are 12–14 cm long and 5–7 cm wide, dark green on the upper surface (5GY 5/10) (FIG. 14) and slightly lighter on the lower surface (5GY 7/4) (FIG. 15). Leaflet margins are entire i.e. no serration. The pubescence on young, unfolding leaves is found on the adaxial and abaxial surfaces as well as on the rachis. The mature leaves are not pubescent and are very smooth. The venation is pinnate.

Figure 16:
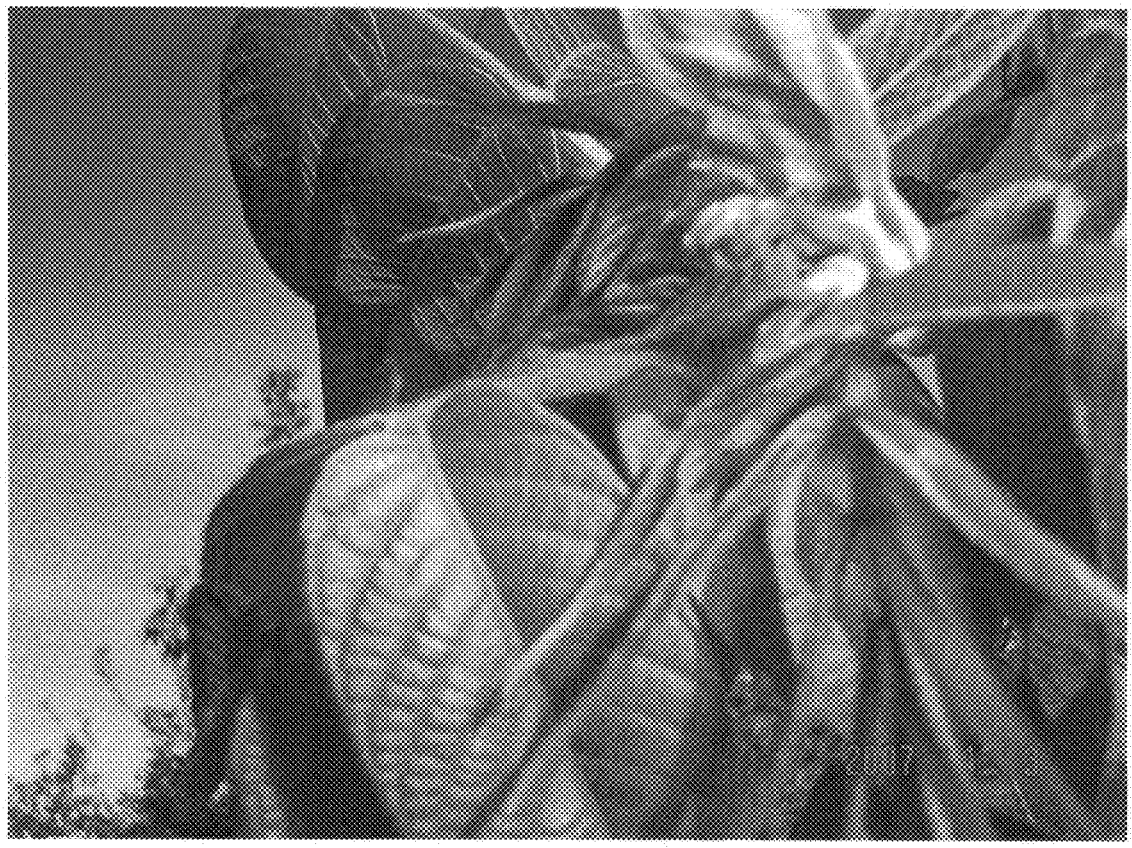
FIG. 16 shows the flower of 'RX1'.

Inflorescence: The flowers are small (2 mm×5 mm) and borne in two or three at the shoot tip (FIG. 16). The stigma surface is red (5R 5/8) and the involucre is green (2.5GY 6/6) covered with sticky hairs. There is no calyx. 'RX1' produces a light crop of nuts.

Disease resistance and susceptibility: This rootstock is more resistant to *Phytophthora citricola* in greenhouse tests than other *Juglans* rootstocks. It is the most resistant variety to *P. citricola* known to the inventors.

Usage: The new rootstock of the present invention provides walnut growers with a new clonally propagated rootstock. It can be easily micropropagated through standard tissure culture micropropagation.

TABLE 1

Clones grown in Stanislaus County, California in 2004

| Clone | Planted N | Graftable N | Graftable % | Diameter (mm) Mean | SD | Range | CV |
|---|---|---|---|---|---|---|---|
| Nematodes | | | | | | | |
| VX211 | 106 | 87 | 82 | 31 | 4.9 | 21-44 | 12.6 |
| Phytophthora | | | | | | | |
| AZ2 | 230 | 151 | 66 | 26 | 5 | 13-38 | 19.2 |
| AZ3 | 49 | 24 | 49 | 25 | 6.7 | 11-37 | 26.8 |
| NZ1 | 172 | 111 | 64 | 26 | 4.4 | 10-39 | 16.9 |
| JX2 | 246 | 191 | 78 | 29 | 4.1 | 13-39 | 14.1 |

TABLE 1-continued

Clones grown in Stanislaus County, California in 2004

| Clone | Planted N | Graftable N | Graftable % | Diameter (mm) Mean | SD | Range | CV |
|---|---|---|---|---|---|---|---|
| RX1 | 104 | 78 | 75 | 18 | 1.6 | 14-22 | 8.8 |
| AX1 | 163 | 86 | 53 | 27 | 4.3 | 14-40 | 15.9 |
| GZ1 | 108 | 83 | 77 | 26 | 5.4 | 13-40 | 20.8 |
| Px1 | 247 | 154 | 62 | 26 | 4.6 | 12-40 | 17.7 |
| AZ1 | 52 | 38 | 73 | 30 | 4.4 | 22-43 | 14.7 |
| UX1 | 27 | 23 | 85 | 25 | 4 | 15-30 | 16 |
| GZ2 | 47 | 38 | 81 | 26 | 4.5 | 15-33 | 17.3 |
| Blackline | | | | | | | |
| WIP3 | 158 | 66 | 42 | 26 | 5 | 12-35 | 19.2 |
| WIP9 | 10 | 6 | 60 | 25 | 2.3 | 23-99 | 9.2 |
| Control | | | | | | | |
| UX022 | 71 | 59 | 83 | 23 | 3.7 | 14-29 | 16.1 |
| English | | | | | | | |
| Vina | 14 | 10 | 71 | 18 | 3.7 | 13-24 | 20.5 |
| Sunland | 64 | 20 | 31 | 26 | 3.8 | 18-31 | 14.6 |
| Totals | 1868 | 1225 | 66 | 25 | | | |

TABLE 2

Clones grown in Butte County, California in 2004.

| Clone | Planted N | Graftable N | Graftable % | Diameter (mm) Mean | SD | Range | CV |
|---|---|---|---|---|---|---|---|
| AX1 | 120 | 107 | 89 | 19 | 4.6 | 10-30 | 26 |
| AZ2 | 120 | 102 | 85 | 21 | 4.7 | 10-31 | 22 |
| RX1 | 120 | 84 | 70 | 19 | 3.2 | 10-27 | 17 |
| Totals | 360 | 293 | 81 | 20 | | | |

TABLE 3

Field performance of clonal Paradox hybrids, Northern California black walnut, and Chinese wingnut rootstocks in non-infested soil and soil infested with *Phytophthora citricola*, Davis.

| Clone (or species) | Maternal background of hybrid (or species of standard) | Soil treatment (January 2006) | Incidence of crown rot (%) |
|---|---|---|---|
| AX1 | *californica* | Control | 0 c |
| | | *P. citricola* | 4 c |
| AZ2 | (*major x hindsii*)*x nigra* | Control | 0 c |
| | | *P. citricola* | 0 c |
| NZ1 | (*major x hindsii*)*x nigra* | Control | 0 c |
| | | *P. citricola* | 0 c |
| GZ1 | *hindsii* | Control | 0 c |
| | | *P. citricola* | 4 c |
| JX2 | *hindsii* | Control | 0 c |
| | | *P. citricola* | 0 c |
| PX1 | *hindsii* | Control | 0 c |
| | | *P. citricola* | 8 c |
| VX211 | *hindsii* | Control | 0 c |
| | | *P. citricola* | 0 c |
| RX1 | *microcarpa* | Control | 0 c |
| | | *P. citricola* | 0 c |
| WIP3 | *hindsii x regia* | Control | 0 c |
| | | *P. citricola* | 8 bc |
| (NCB) | (*J. hindsii*) | Control | 16 b |
| | | *P. citricola* | 62 a |
| (Wingnut) | (*Pt. stenopiera*) | Control | 0 c |
| | | *P. citricola* | 0 c |

TABLE 3-continued

Field performance of clonal Paradox hybrids, Northern California black walnut, and Chinese wingnut rootstocks in non-infested soil and soil infested with *Phytophthora citricola*, Davis.

| Clone (or species) | Percent of trunk circ. Necrotic | Incidence of tree mortality % | Increase in trunk circ. (mm) |
|---|---|---|---|
| AX1 | 0 c | 0 c | 163 c |
| | 1 c | 0 c | 146 cde |
| AZ2 | 0 c | 0 c | 116 fg |
| | 0 c | 0 c | 117 fg |
| NZ1 | 0 c | 0 c | 116 fg |
| | 0 c | 0 c | 130 def |
| GZ1 | 0 c | 0 c | 157 cd |
| | 1 c | 0 c | 150 cd |
| JX2 | 0 c | 0 c | 166 bc |
| | 0 c | 0 c | 135 def |
| PX1 | 0 c | 0 c | 169 bc |
| | 1 c | 0 c | 157 cd |
| VX211 | 0 c | 0 c | 191 b |
| | 0 c | 0 c | 147 cde |
| RX1 | 0 c | 0 c | 112 fg |
| | 0 c | 0 c | 116 fg |
| WIP3 | 0 c | 0 c | 100 g |
| | 2 c | 0 c | 121 efg |
| (NCB) | 17 b | 17 b | 68 h |
| | 59 a | 59 a | 57 h |
| (Wingnut) | 0 b | 0 e | 226 a |
| | 0 b | 0 c | 193 b |

[2]All trees were planted May 2005. The assements of crown rot and mortality were made Nov. 21, 2006. Means within a column and without letters in common are significantly different (Waller k ratio).

What we claim is:

1. A new and distinct variety of walnut rootstock plant designated 'RX1' as shown and described herein.

* * * * *